(12) United States Patent
Choi et al.

(10) Patent No.: US 10,634,798 B2
(45) Date of Patent: Apr. 28, 2020

(54) RADIATION APPARATUS AND RADIATION SIGNAL PROCESSING METHOD USING BIPOLAR TIME-OVER-THRESHOLD METHOD

(71) Applicant: Sogang University Research & Business Development Foundation, Seoul (KR)

(72) Inventors: Yong Choi, Seoul (KR); Ji Woong Jung, Seoul (KR)

(73) Assignee: SOGANG UNIVERSITY RESEARCH & BUSINESS DEVELOPMENT FOUNDATION, Seoul (KR)

(*) Notice: Subject to any disclaimer, the term of this patent is extended or adjusted under 35 U.S.C. 154(b) by 481 days.

(21) Appl. No.: 15/697,578

(22) Filed: Sep. 7, 2017

(65) Prior Publication Data

US 2018/0011204 A1    Jan. 11, 2018

Related U.S. Application Data

(63) Continuation of application No. PCT/KR2016/003795, filed on Apr. 11, 2016.

(30) Foreign Application Priority Data

Apr. 10, 2015    (KR) .................... 10-2015-0050876

(51) Int. Cl.
  *G01T 1/16*    (2006.01)
  *A61B 6/00*    (2006.01)
  *H03M 1/50*    (2006.01)

(52) U.S. Cl.
  CPC ............ *G01T 1/16* (2013.01); *A61B 6/00* (2013.01); *H03M 1/50* (2013.01)

(58) Field of Classification Search
  CPC .............. G01T 1/16; A61B 6/00; H03M 1/50
  See application file for complete search history.

(56) References Cited

U.S. PATENT DOCUMENTS

2010/0025589 A1    2/2010    Olcott
2012/0114033 A1    5/2012    Chen
(Continued)

FOREIGN PATENT DOCUMENTS

JP    2001-051062 A    2/2001
JP    2013-029361 A    2/2016

OTHER PUBLICATIONS

Kim, et al., "A New Multiplexing Method Using Multi-Voltage Threshold Based PET DAQ With FPGA and Exclusive-OR Logic Gate", IEEE 2013 Nuclear Science Symposium and Medical Imaging Conference, 2013.
(Continued)

*Primary Examiner* — Curtis B Odom
(74) *Attorney, Agent, or Firm* — Pearne & Gordon LLP

(57) ABSTRACT

A radiation apparatus and a radiation signal processing method are provided. To elaborate, the apparatus includes an input unit including a radiation detector; an amplification unit configured to amplify a signal input through the radiation detector; a bipolar signal generation unit configured to generate a bipolar signal by converting the amplified signal; and a comparison unit configured to output a digital signal on the basis of comparison results of the bipolar signal with a preset first threshold value and a preset second threshold value. Herein, the comparison unit includes a first comparator configured to output a digital pulse in an interval where the bipolar signal is larger than the first threshold value and a second comparator configured to output a digital pulse in an interval where the bipolar signal is smaller than the second threshold value.

14 Claims, 6 Drawing Sheets

(56) References Cited

U.S. PATENT DOCUMENTS

2012/0275549 A1 11/2012 Crepaldi
2016/0170037 A1* 6/2016 Katsuyama ............... G01T 1/17
　　　　　　　　　　　　　　　　　　　　　250/336.1

OTHER PUBLICATIONS

International Search Report for PCT/KR2016/003795 dated Jul. 25, 2016.

* cited by examiner

RADIATION APPARATUS AND RADIATION SIGNAL PROCESSING METHOD USING BIPOLAR TIME-OVER-THRESHOLD METHOD

CROSS-REFERENCE TO RELATED APPLICATION

This application claims priority to and the benefit of PCT Patent Application No. PCT/KR2016/003795 filed on Apr. 11, 2016, and Korean Patent Application No. 10-2015-0050876 filed on Apr. 10, 2015, the entire disclosures of which are incorporated herein by reference.

BACKGROUND

1. Field

The present disclosure relates to an apparatus and a method for processing radiation signal by using a time-over-threshold (TOT) method of obtaining energy and time information of radiation-detected from a medical radiation imaging device.

2. Description of Related Art

In general, a signal processing system of a medical radiation imaging device analyzes energy and time information of detected radiation using an analog-to-digital converter and a time-to-digital converter, respectively. Since the medical radiation imaging device including multiple detectors needs to analyze a lot of information, it is configured as a complicated signal processing system including many converters.

Meanwhile, in a signal processing method using a recently appearing TOT method, a threshold voltage is previously set in a comparator and then, energy and time information of a digital signal output from the comparator are analyzed using a time-to-digital converter.

In this signal processing method using the TOT method, a signal processing system can be constructed without using an analog-to-digital converter.

The TOT method is set the threshold voltage on the comparator and, then the energy and time information of the gamma ray is calculated the time width of the acquired digital signal by the comparator. Specifically, as a signal processing method using a conventional TOT method, a method of setting a threshold voltage in a comparator and computing a width and a starting time of a digital signal generated by inducing a change in digital signal width caused by an analog signal transition to analyze radiation energy and time information has been suggested. However, the signal processing method using the conventional TOT method has the nonlinear relationship of the pulse amplitude of detected signal to the measured TOT time width conversion.

In this regard, U.S. Patent Laid-open Publication No. 2010-0025589 (entitled "High energy photon detection using pulse width modulation") discloses a technology of improving linearity by changing a width of a digital signal with respect to an analog signal detected through a high-energy photon detector.

SUMMARY

Some exemplary embodiments of the present disclosure provide a radiation apparatus and method of analyzing energy and time information of the radiation by changing a unipolar analog signal into a bipolar analog signal and converting the changed signal into a digital signal using a time-over-threshold method.

However, problems to be solved by the present disclosure are not limited to the above-described problems. There may be other problems to be solved by the present disclosure.

According to an exemplary embodiment of the present disclosure, a radiation signal processing method includes: receiving an input of a radiation signal; amplifying the input signal; generating a bipolar signal by converting the amplified signal from a unipolar to a bipolar; and outputting a digital signal on the basis of comparison results of the bipolar signal with a preset first threshold value and a preset second threshold value. Herein, in the outputting of the digital signal, two digital pulses are output in an interval where the bipolar signal is larger than the first threshold value and an interval where the bipolar signal is smaller than the second threshold value, respectively.

According to another exemplary embodiment of the present disclosure, a radiation apparatus includes: an input unit including a radiation detector; an amplification unit configured to amplify a signal input through the radiation detector; a bipolar signal generation unit configured to generate a bipolar signal by converting the amplified signal from a unipolar to a bipolar; and a comparison unit configured to output a digital signal on the basis of comparison results of the bipolar signal with a preset first threshold value and a preset second threshold value. The comparison unit includes a first comparator configured to output a digital pulse in an interval where the bipolar signal is larger than the first threshold value and a second comparator configured to output a digital pulse in an interval where the bipolar signal is smaller than the second threshold value. Further, energy and time information of the radiation are obtained by computing the widths and starting times of digital signals output through the first comparator and the second comparator.

According to any one of the above-described aspects of the present disclosure, by changing a radiation signal which is a unipolar analog signal into a bipolar signal including a (+) V potential signal having a fast rise time and a (−) V potential signal having a linear fall time and then computing widths of two digital signals generated by a preset threshold voltage, energy and time information of a radiation are obtained. Thus, it is possible to provide a radiation signal processing method which is simple and economically excellent as compared with a conventional signal processing method. Further, according to any one of the aspects of the present disclosure, enhanced time resolution can be provided using the (+) V potential signal having a fast rise time as compared with a conventional TOT signal processing system, and a signal process with excellent linearity can be performed using the (−) V potential signal having a linear fall time.

DETAILED DESCRIPTION

Figure 1:
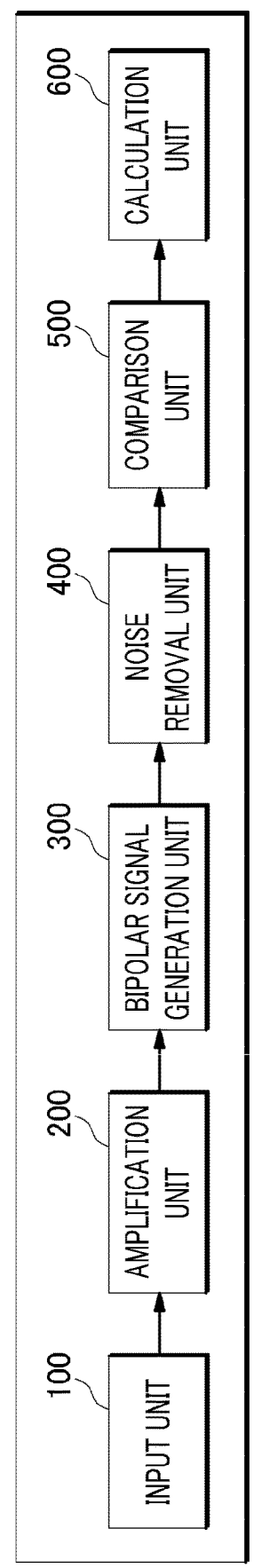
FIG. 1 is a block diagram of a radiation apparatus in accordance with an exemplary embodiment of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Hereinafter, a radiation apparatus and a radiation signal processing method thereof in accordance with an exemplary embodiment of the present disclosure will be described in detail with reference to the accompanying drawings.

FIG. 1 is a block diagram of a radiation apparatus in accordance with an exemplary embodiment of the present disclosure.

Referring to FIG. 1, a radiation apparatus 10 includes an input unit 100, an amplification unit 200, a bipolar signal generation unit 300, a noise removal unit 400, a comparison unit 500, and a calculation unit 600.

The input unit 100 may include a radiation detector and receives an input of a detected radiation signal. In general, a radioactive decayable atomic nucleus is called "radionuclide". The decay of the radionuclide is roughly classified into three types: alpha (α) decay in which an alpha (α) particles is emitted; beta ($\beta^\pm$) decay in which a beta ($\beta^\pm$) particle is emitted; and gamma (γ) decay in which a gamma (γ)-ray is emitted. The input unit 100 may process at least one of radiation signals of an X-ray, a γ-ray, and an α-ray. In an exemplary embodiment of the present disclosure, a γ-ray signal processing by the input unit 100 will be described as an example. Further, a photomultiplier, a semiconductor detector, or a semiconductor photo sensor may be used as the input unit 100.

The amplification unit 200 amplifies the signal input from the input unit 100. An amplification unit using an operational amplifier and a transistor may be used as the amplifier 200. In this case, the amplification unit 200 may include a feedback path connected between an inverting input terminal and an output terminal of the operational amplifier.

The bipolar signal generation unit 300 generates a bipolar signal by converting the analog signal amplified by the amplification unit 200 from a unipolar to a bipolar. In this case, a high-pass filter suitable for the purpose of use may be used as the bipolar signal generation unit 300. The bipolar signal generation unit 300 removes a low-frequency component but allows a high-frequency component to pass through using the high-pass filter to change the unipolar signal into a bipolar signal including a (+) V potential signal having a fast rise time and a (−) V potential signal having a linear fall time.

For reference, bipolarity is a term distinguished from unipolarity and refers to an input signal with different voltage polarities. That is, a bipolar signal has three potentials of 0 V, (−) V, and (+) V. If a data value is 0, the bipolar signal has 0 V, and if a data value is 1, the bipolar signal has (−) V and (+) V values alternately.

Further, the bipolar signal generation unit 300 adjusts a voltage level of a base portion of the amplified signal. Particularly, the bipolar signal generation unit 300 can increase a voltage level overall. Also, in some cases, the bipolar signal generation unit 300 can switch a voltage polarity.

The noise removal unit 400 removes a noise of the generated bipolar signal. A low-pass filter or a band-pass filter may be used as the noise removal unit 400 to filter a frequency band in a specific domain of the bipolar signal. In this case, the noise removal unit 400 may allow only a low-frequency signal to pass through using the low-pass filter or the band-pass filter and remove a noise signal component out of an operating frequency band of a radiation signal processing system.

The comparison unit 500 outputs a digital pulse on the basis of comparison results of the bipolar signal from which the noise is removed with a first threshold value and a second threshold value. In this case, the comparison unit 500 includes a first comparator that outputs a digital pulse (e.g., a high-level digital pulse) by comparison with an interval where the bipolar signal is larger than the first threshold value, and a second comparator that outputs a digital pulse (e.g., a high-level digital pulse) by comparison with an interval where the bipolar signal is smaller than the second threshold value.

The calculation unit 600 calculates time widths of the digital signal output from the comparison unit 500. In this case, the calculated time width of the digital signal indicates energy information of the radiation. In a conventional TOT signal processing method, energy information has been computed using a time width of a single digital signal, whereas in the radiation signal processing method according to an exemplary embodiment of the present disclosure, energy information is analyzed using time widths of two digital signals.

Further, the calculation unit 600 calculates an output time of the digital pulse output in the interval where the bipolar signal is larger than the first threshold value and an output time of the digital pulse output in the interval where the bipolar signal is smaller than the second threshold value. In this case, the calculation unit 600 calculates detection energy of an incident radiation from the sum of the calculated output times of the respective digital pulses. That is, a time width of radiation detection indicates detection energy. Also, the calculation unit 600 may specify a detection time as a starting point of radiation detection on the basis of a starting time of the digital pulse output from the first comparator.

Hereinafter, the above-described matters will be described in more detail with reference to FIG. 2 and FIGS. 3a-e.

Figure 2:
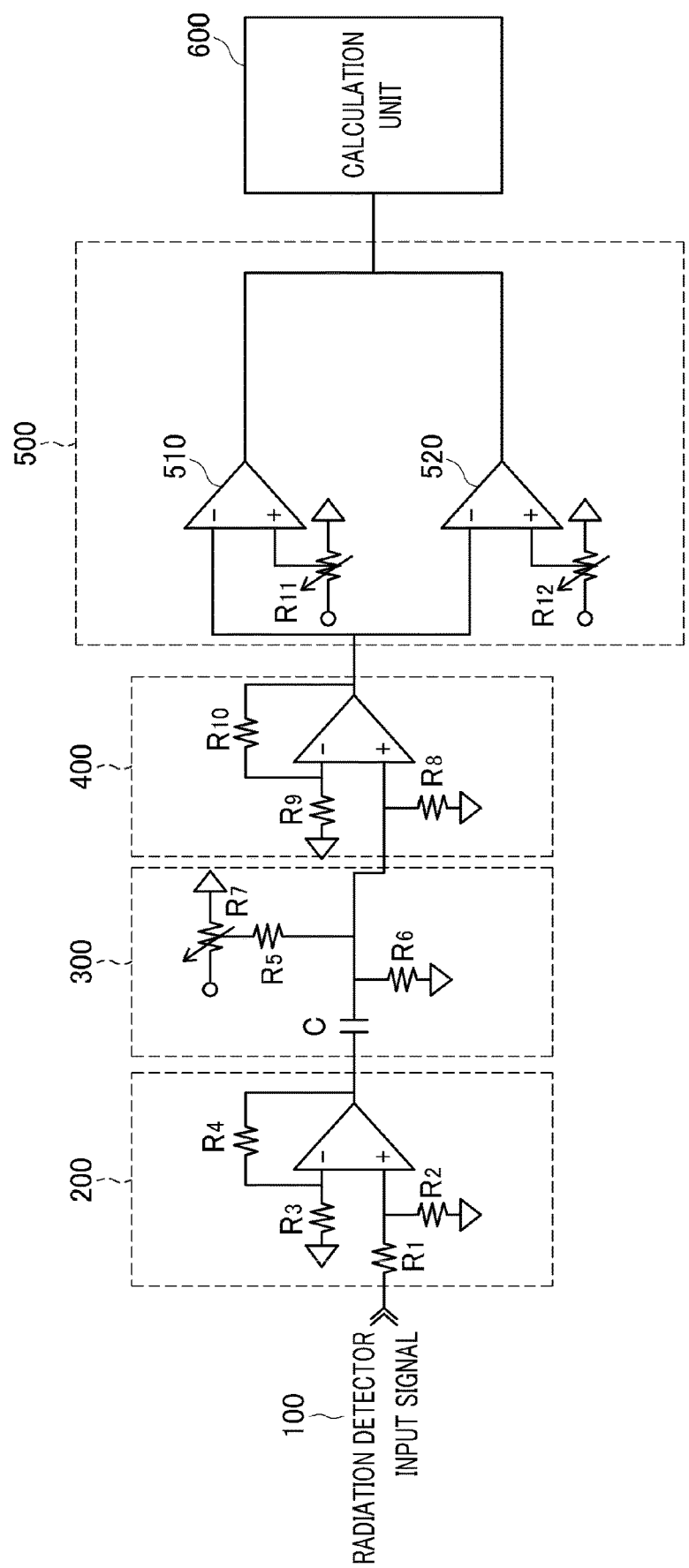
FIG. 2 is a circuit diagram of a radiation apparatus in accordance with an exemplary embodiment of the present disclosure.

FIG. 2 is a circuit diagram of a radiation apparatus in accordance with an exemplary embodiment of the present disclosure.

Further, FIGS. 3a-e shows exemplary diagrams of radiation signals respectively generated from stages of a circuit of a radiation apparatus in accordance with an exemplary embodiment of the present disclosure.

Figure 3:
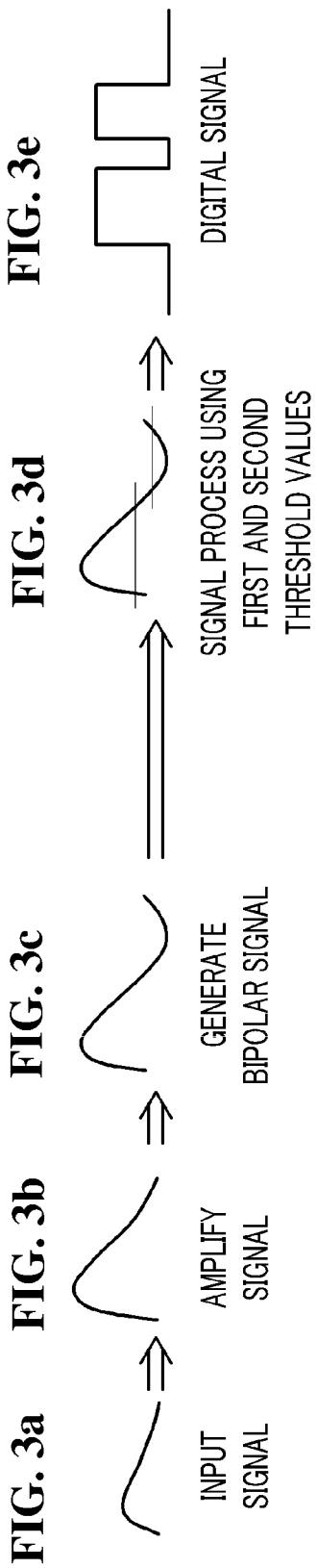
FIGS. 3a-e show exemplary diagrams of radiation signals respectively generated from stages of a circuit of a radiation apparatus in accordance with an exemplary embodiment of the present disclosure.

Referring to FIG. 2, a radiation signal input through the input unit 100 (e.g., a photomultiplier, a semiconductor detector, or a semiconductor photo sensor) is input into the amplification unit 200. In this case, the input signal may have a shape as shown in FIG. 3a.

In this case, the amplification unit 200 may be installed in back of the detector (i.e., input unit 100) in order to suppress signal attenuation caused by an electric wire or a decrease in signal to noise ratio caused by an exogenous noise, and such an amplifier is called "preamplifier".

Then, the amplification unit 20 may amplify the signal using an operational amplifier and a transistor. In FIG. 2, an operational amplifier is illustrated as an example of the amplification unit 200. As shown in FIG. 2, a non-inverting input terminal of the operational amplifier 200 is connected to a resistance R1 of which one end is connected to the input unit 100 and a resistance R2 connected between the other end of the resistance R1 and the ground. In this case, an impedance matching between the radiation detector (i.e., input unit 100) and the amplification unit 200 can be performed by adjusting values of the resistance R1 and the resistance R2. Further, an inverting input terminal of the operational amplifier 200 is connected to a resistance R3 of which one end is connected to the ground and a resistance R4 connected to the other end of the resistance R3. In this case, the resistance R4 serves as a feedback element configured to connect the inverting input terminal and the bipolar signal generation unit 300 and adjusts an amplification factor. The signal passing through the preamplifier has an amplified shape as shown in FIG. 3b.

Then, the amplified signal passes through the bipolar signal generation unit 300, and in this case, a voltage level of the amplified signal is adjusted. As shown in FIG. 2, the bipolar signal generation unit 300 includes a capacitor C and resistances connected in parallel to the capacitor C. Specifically, one terminal of the capacitor C is connected to an output end of the amplification unit 200, and the other terminal of the capacitor C is connected to a resistance R6 and a resistance R5 connected to a variable resistance R7. In this case, the capacitor C may collect charges and the variable resistance R7 may adjust the amount of current. If the capacitor C and the resistance R5 of the bipolar signal generation unit 300 function as a high-pass filter, a bipolar signal is generated by this filter. Further, the bipolar signal generation unit 300 may adjust a base voltage in order for all of signals to be positive signals. In this case, a positive voltage supplied by the resistance R6 and the resistance R7 may be added to an output end signal of the filter including the capacitor C and the resistance R5. As such, the signal converted by the bipolar signal generation unit 300 may have a shape as shown in FIG. 3c.

Then, a noise of the bipolar signal is removed by the noise removal unit 400. FIG. 2 illustrates that a low-pass filter or a band-pass filter is used as the noise removal unit 400. The low-pass filter may remove a high-frequency signal corresponding to a noise. As illustrated in FIG. 2, the noise removal unit 400 includes an operational amplifier and resistances R8, R9, and R10. In this case, a non-inverting input terminal of the operational amplifier is connected to an output end of the bipolar signal generation unit 300 and the resistance R8 is connected between the inverting input terminal of the operational amplifier and the ground. Further, an inverting input terminal of the operational amplifier is connected to one end of the resistance R9 of which the other end is connected to the ground and one end of the resistance R10. Furthermore, the other end of the resistance R10 is connected to an output end of the operational amplifier. In this case, the resistance R10 functions as a feedback element configured to connect the inverting terminal and the output end. As such, the signal passing through the noise removal unit 400 is input into the comparison unit 500.

Then, the comparison unit 500 outputs a digital pulse on the basis of comparison results of the bipolar signal from which the noise is removed with a first threshold value and a second threshold value. Referring to FIG. 2, the comparison unit 500 includes a first comparator 510 and a second comparator 520, and the first and second comparators 510 and 520 may separately process the signal. Referring to FIG. 3d, it can be seen that when processing the bipolar signal, the first threshold value and the second threshold value are applied. Specifically, an interval where the bipolar signal is larger than the first threshold value is processed through the first comparator 510 of which a signal line connected to an output end of the noise removal unit 400 is input into a non-inverting input terminal. Also, an interval where the bipolar signal is smaller than the second threshold value is processed through the second comparator 510 of which a signal line connected to the output end of the noise removal unit 400 is connected to an inverting input terminal. In this case, the first threshold value is higher than the second threshold value.

A voltage of the first threshold value is applied to the non-inverting input terminal of the first comparator 510. In this case, the voltage of the first threshold value may be set by a variable resistance R11 connected to the non-inverting input terminal of the first comparator 510. Also, a voltage of the second threshold value is applied to a non-inverting input terminal of the second comparator 520. In this case, the voltage of the second threshold value may be set by a variable resistance R12 connected to the non-inverting input terminal of the second comparator 520. That is, the first threshold value and the second threshold value may be adjusted by the variable resistances R11 and R12, respectively.

In the configuration described above, the first comparator 510 outputs a digital pulse in the interval where the bipolar signal is larger than the first threshold value and the second comparator 520 outputs second digital pulse in the interval where the bipolar signal is smaller than the second threshold value.

Then, the calculation unit 600 computes a value of the digital pulse output in the interval where the bipolar signal is larger than the first threshold value with a time-to-digital converter and computes a value of the digital pulse output in the interval where the bipolar signal is smaller than the second threshold value with the time-to-digital converter. In this case, energy information depending on a time width is obtained by adding up the converted time values and time information is obtained using a starting point of a first digital pulse value (see FIG. 3e). Thus, energy and time information of the radiation can be calculated.

That is, if two digital pulses are output due to the first and second threshold values, detection energy may be calculated by computing widths of maintenance times of the two output digital pulses and a detection time of an incident radiation may be detected by measuring a starting point of the first digital pulse.

The above-described digital signal processing method will be described in more detail with reference to FIG. 4.

Figure 4:
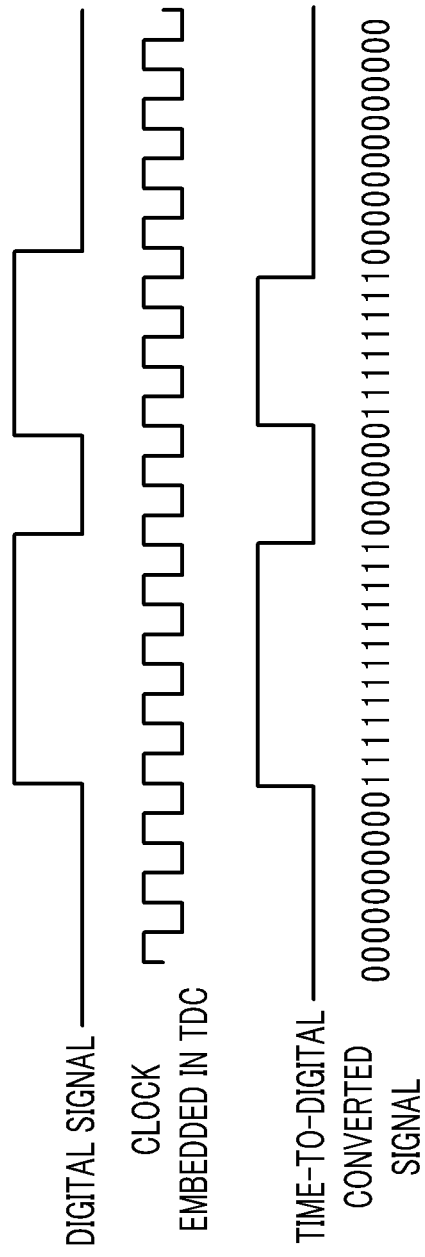
FIG. 4 is a conceptual diagram provided to explain a digital signal processing method during a radiation signal process in accordance with an exemplary embodiment of the present disclosure.

FIG. 4 is a conceptual diagram provided to explain a digital signal processing method during a radiation signal process in accordance with an exemplary embodiment of the present disclosure.

For reference, a time-to-digital converter (TDC) can measure a time width of two digital signals on the basis of a clock signal output according to a predetermined cycle. For example, as shown in FIG. 4, a time width of each digital pulse can be calculated by accumulating and adding up each of the number of clock signals (i.e., four) output while a first digital pulse of the digital signal is maintained and the number of clock signals (i.e., three) output while a second digital pulse is maintained.

Figure 5:
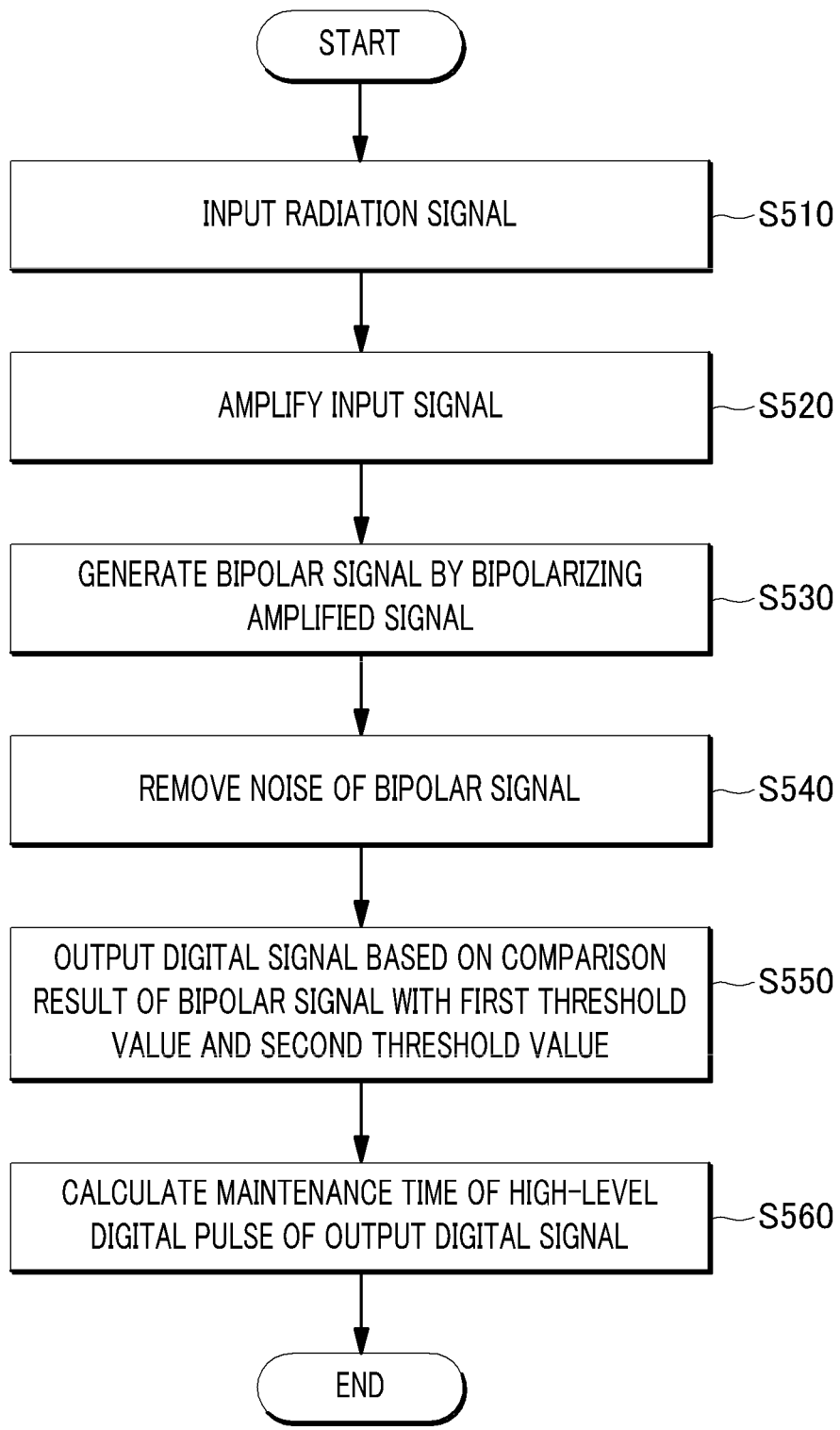
FIG. 5 is a flowchart provided to explain a radiation signal processing method in accordance with an exemplary embodiment of the present disclosure.

FIG. 5 is a flowchart provided to explain a radiation signal processing method in accordance with an exemplary embodiment of the present disclosure.

The radiation signal processing method according to an exemplary embodiment of the present disclosure includes receiving an input of a radiation signal (S510), amplifying the input signal (S520), generating a bipolar signal by converting the amplified signal from a unipolar to a bipolar (S530), and outputting a digital signal on the basis of comparison results of the bipolar signal with a first threshold value and a second threshold value (S550). In this case, the radiation signal processing method may further include removing a noise of the bipolar signal (S540) after the generating of the bipolar signal.

Furthermore, the radiation signal processing method may include calculating a time width of a digital pulse (S560) output when outputting the digital signal (S550).

In this case, the calculating of the time width of the digital pulse (S560) may include calculating an output time of a digital pulse output in an interval where the bipolar signal is larger than the first threshold value; calculating an output time of a digital pulse output in an interval where the bipolar signal is smaller than the second threshold value, and calculating detection energy of an input radiation from the sum of the calculated output times of the respective digital pulses. Also, a detection time as a starting point of radiation detection can be specified on the basis of an output start time of the digital pulse output in the interval where the bipolar signal is larger than the first threshold value.

More specifically, the radiation apparatus 10 receives a radiation signal (S510). In this case, the measured radiation signal is input into the input unit 100 of the radiation signal processing system.

A radiation signal can be measured with various devices. For example, a radiation signal may be measured using a radiation counter. In this case, if a radiation reaches a scintillator within the radiation counter, electrons or positrons generated via interactions such as photoelectric effect, Compton effect, and electron-pair production may be excited and generated and then detected by spectra. Also, if a radiation signal is measured using a gas detector and a semiconductor detector, the radiation signal may be measured by obtaining an electron via an ionization reaction in which when a radiation passes through a material, an atom or a molecule of the material is ionized and thus an ion is generated.

Then, the radiation apparatus 10 amplifies the signal (S520) input in the previous step S510. In this case, the input signal may be amplified in the amplification unit 200. The amplification unit 20 may be aligned such that a single amplification unit corresponds to a single signal line. An amplifier of the amplification unit 200 may include a voltage amplifier and a current amplifier (or charge-sensitive amplifier).

Then, the radiation apparatus 10 generates a bipolar signal by converting the signal (S530) amplified in the previous step S520. In this case, the amplified signal (i.e., unipolar signal) may be changed into the bipolar signal including a (+) V potential signal having a fast rise time and a (−) V potential signal having a linear fall time by a high-pass filter of the bipolar signal generation unit 300. Also, the bipolar signal generation unit 300 may adjust a voltage level of a base portion of the amplified signal.

Then, the radiation apparatus 10 removes a noise of the bipolar signal (S540) generated in the previous step S530. In this case, the noise removal unit 400 may filter a frequency band in a specific domain of the bipolar signal using a low-pass filter and a band-pass filter.

As such, if the removing of the noise (S540) is performed, it is possible to limit a frequency range of the bipolar signal or remove an unnecessary transient response signal. In some cases, the removing of the noise (S540) can be omitted.

Then, the radiation apparatus 10 outputs a digital signal (S550) on the basis of comparison results of the bipolar signal from which the noise is removed in the previous step S540 with preset first and second threshold values.

In this case, when outputting the digital signal (S550), two digital pulses are output in an interval where the bipolar signal is larger than the first threshold value and an interval where the bipolar signal is smaller than the second threshold value, respectively.

Then, the radiation apparatus 10 calculates time widths of the digital pulses (S560) output in the previous step S550. In this case, time widths corresponding to the maintenance times of the digital pulses can be calculated and starting times (i.e., starting points) of the digital pulses can be measured. Thus, it is possible to check energy information depending on a time width and time information depending on a starting point.

FIGS. 6a-d show exemplary diagrams illustrating the results of a radiation (e.g., gamma ray) signal process through a radiation apparatus in accordance with an exemplary embodiment of the present disclosure.

Figure 6A:
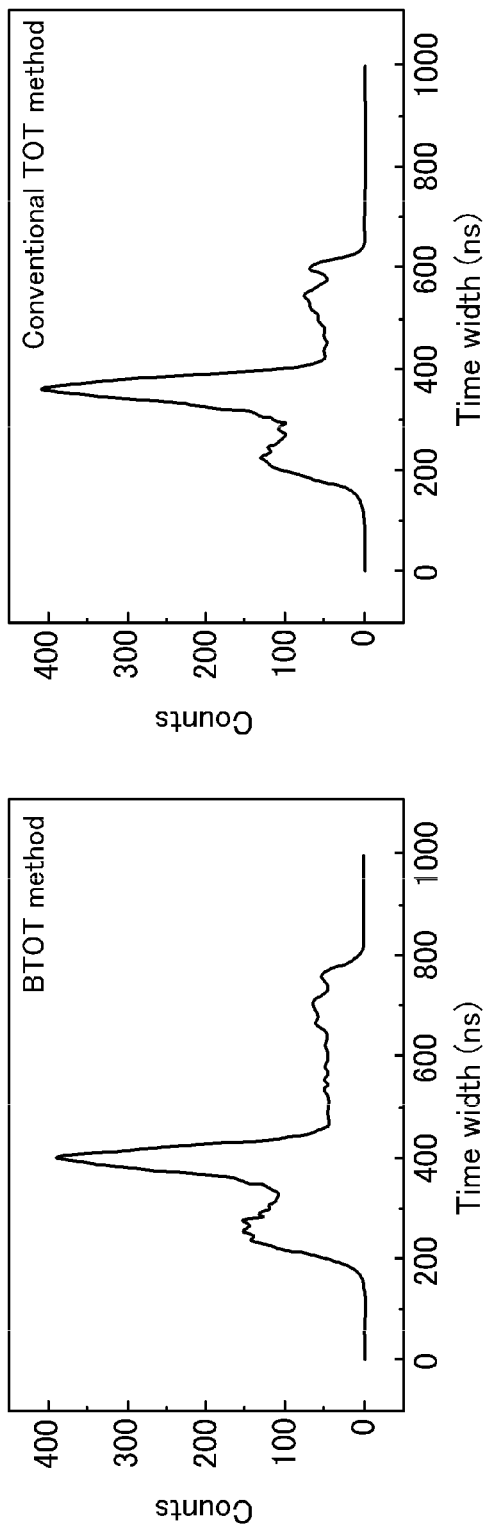
FIGS. 6a-d show exemplary diagrams illustrating the results of a radiation signal process through a radiation apparatus in accordance with an exemplary embodiment of the present disclosure.
Figure 6B:
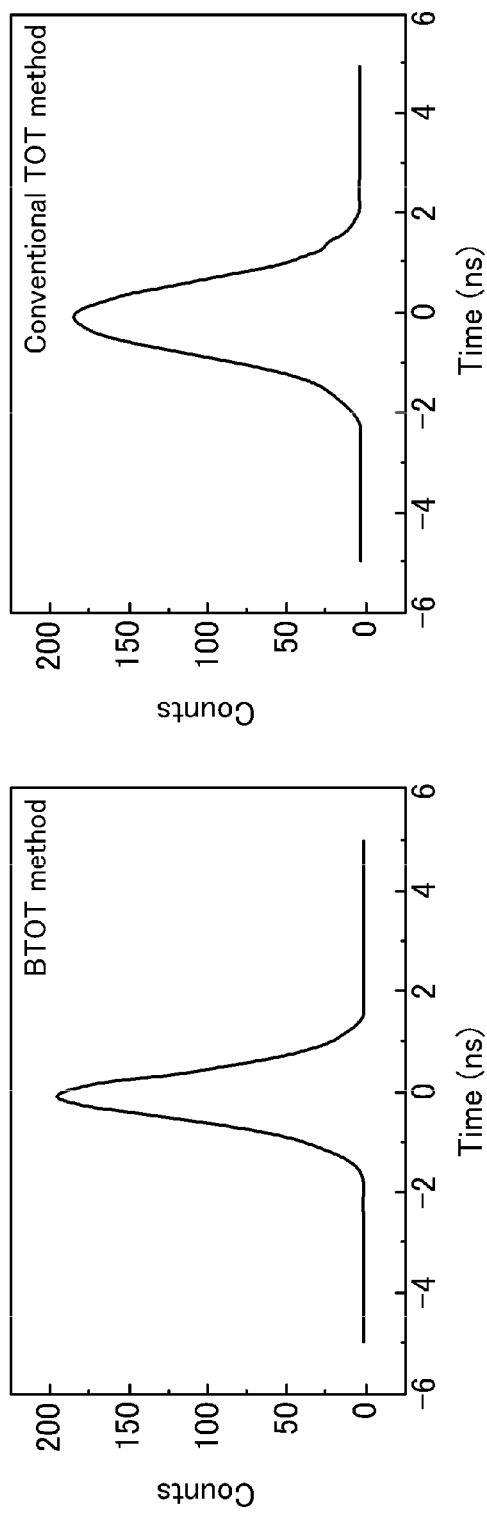
Figure 6C:
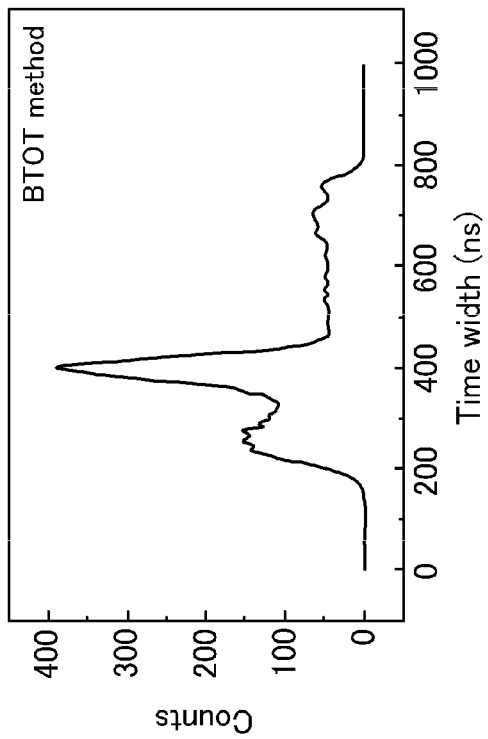
Figure 6D:
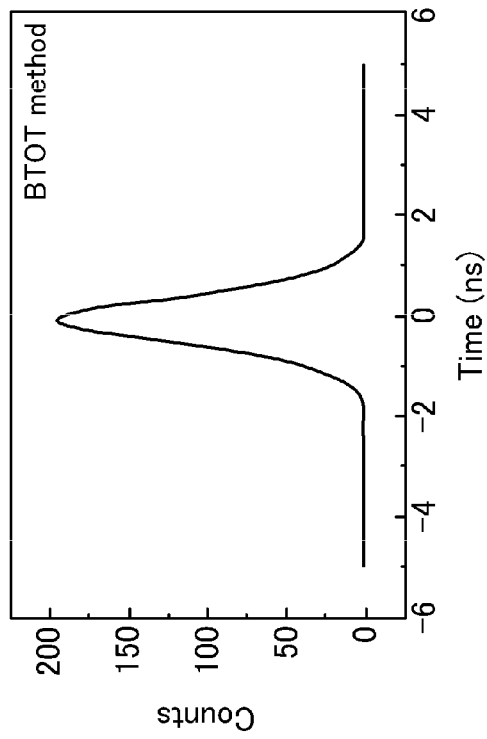

The graphs of illustration of FIGS. 6a and 6c show the results of a signal process through the radiation apparatus 10 according to an exemplary embodiment of the present disclosure, and the graphs of illustration of FIGS. 6b and 6d show the results of a signal process according to the conventional TOT method. By comparison between the graphs of illustration of FIGS. 6a and 6b, it can be seen that linearity with respect to different energy levels is excellent in the graph of illustration of FIG. 6a. By comparison between the graphs of illustration of FIGS. 6c and 6d, it can be seen that the graph of illustration of FIG. 6c has a shape with a narrower width based on 0. Accordingly, it is confirmed that the signal process through the radiation apparatus according to an exemplary embodiment of the present disclosure provides enhanced time resolution.

Meanwhile, the radiation apparatus and the radiation signal processing method according to an exemplary embodiment of the present disclosure can be applied to various detectors configured to process a radiation signal. For example, a positron emission tomography (PET) imaging device configured to detect a gamma-ray injects a radioisotope into a target object and detects a gamma-ray emitted from a lesion, and a detector used in this case may convert the gamma-ray emitted from the target object into a visible ray and then convert the visible ray into an electric signal. A gamma-ray signal can be processed by applying a circuit of the radiation apparatus using the TOT method according to an exemplary embodiment of the present disclosure to the detector, and, thus, it is possible to check energy and time information.

Further, the radiation apparatus and the radiation signal processing method according to an exemplary embodiment of the present disclosure can also be used for a method of detecting an X-ray. For example, an X-ray CT (Computed Tomography) imaging device irradiates an X-ray to a target object and generates an image using an attenuation ratio of the X-ray passing through the target object, and a detector used in this case may function to convert the X-ray into a visible ray and then into an electric signal. An X-ray can be processed by applying a circuit of the radiation apparatus using the TOT method according to an exemplary embodiment of the present disclosure to the detector, and, thus, it is possible to obtain a signal with excellent linearity as compared with a signal process employing the conventional TOT method.

Besides, the radiation apparatus and the radiation signal processing method using the TOT method according to an exemplary embodiment of the present disclosure can be applied to various detectors, such as a gamma camera and a single-photon tomography, configured to process a gamma ray signal.

The embodiment of the present disclosure can be embodied in a storage medium including instruction codes executable by a computer such as a program module executed by the computer. Besides, the data structure in accordance with the embodiment of the present disclosure can be stored in the storage medium executable by the computer. A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The system and method of the present disclosure has been explained in relation to a specific embodiment, but its components or a part or all of its operations can be embodied by using a computer system having general-purpose hardware architecture.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A radiation signal processing method comprising:
   receiving an input of a radiation signal;
   amplifying the input signal;
   generating a bipolar signal by converting the amplified signal from a unipolar to a bipolar; and
   outputting a digital signal on the basis of comparison results of the bipolar signal with a preset first threshold value and a preset second threshold value,
   wherein in the outputting of the digital signal, two digital pulses are output in an interval where the bipolar signal is larger than the first threshold value and an interval where the bipolar signal is smaller than the second threshold value, respectively.

2. The radiation signal processing method of claim 1, wherein the step of generating the bipolar signal includes adjusting a voltage level of a base portion of the amplified signal.

3. The radiation signal processing method of claim 1, further comprising:
   removing a noise from the generated bipolar signal.

4. The radiation signal processing method of claim 3, wherein in the step of removing the noise, a frequency band in a specific domain of the generated bipolar signal is filtered using a low-pass filter or a band-pass filter.

5. The radiation signal processing method of claim 1, further comprising:
   calculating time widths of the two digital pulses.

6. The radiation signal processing method of claim 5, wherein the step of calculating the time widths of the two digital pulses includes:
   calculating an output time of the digital pulse output in the interval where the bipolar signal is larger than the first threshold value;
   calculating an output time of the digital pulse output in the interval where the bipolar signal is smaller than the second threshold value; and
   calculating detection energy of an incident radiation by adding up the calculated output times of the respective digital pulses.

7. The radiation signal processing method of claim 6, wherein the step of calculating the time widths of the two digital pulses further includes:
   specifying a detection time indicating a starting point of radiation detection on the basis of an output start time of the digital pulse output in the interval where the bipolar signal is larger than the first threshold value.

8. A radiation apparatus comprising:
   an input unit including a radiation detector;
   an amplification unit configured to amplify a signal input through the radiation detector;
   a bipolar signal generation unit configured to generate a bipolar signal by converting the amplified signal from a unipolar to a bipolar; and
   a comparison unit configured to output a digital signal on the basis of comparison results of the bipolar signal with a preset first threshold value and a preset second threshold value,
   wherein the comparison unit includes a first comparator configured to output a digital pulse in an interval where the bipolar signal is larger than the first threshold value and a second comparator configured to output a digital pulse in an interval where the bipolar signal is smaller than the second threshold value.

9. The radiation apparatus of claim 8,
wherein the bipolar signal is applied to a non-inverting terminal of the first comparator and a voltage corresponding to the first threshold value is applied to an inverting terminal of the first comparator, and
the bipolar signal is applied to an inverting terminal of the second comparator and a voltage corresponding to the second threshold value is applied to a non-inverting terminal of the second comparator.

10. The radiation apparatus of claim 8, further comprising:
a noise removal unit configured to remove a noise from the generated bipolar signal.

11. The radiation apparatus of claim 10,
wherein the noise removal unit filters a frequency band in a specific domain of the generated bipolar signal using a low-pass filter or a band-pass filter.

12. The radiation apparatus of claim 8, further comprising:
a calculation unit configured to calculate time widths of two digital pulses output through the comparison unit.

13. The radiation apparatus of claim 12,
wherein the calculation unit calculates an output time of the digital pulse output in the interval where the bipolar signal is larger than the first threshold value,
calculates an output time of the digital pulse output in the interval where the bipolar signal is smaller than the second threshold value, and
calculates detection energy of an incident radiation by adding up the calculated output times of the respective two digital pulses.

14. The radiation apparatus of claim 13,
wherein the calculation unit specifies a radiation detection time indicating a starting point of radiation detection on the basis of an output start time of the digital pulse output in the interval where the bipolar signal is larger than the first threshold value.

* * * * *